United States Patent
Huang et al.

(10) Patent No.: US 11,535,609 B2
(45) Date of Patent: Dec. 27, 2022

(54) PYRAZINE-2(1H)-KETONE COMPOUND PREPARATION METHOD

(71) Applicant: ZHANGZHOU PIEN TZE HUANG PHARMACEUTICAL CO., LTD., Fujian (CN)

(72) Inventors: Jinming Huang, Zhangzhou (CN); Juan Yu, Zhangzhou (CN); Jinxia Lin, Zhangzhou (CN); Limei Yang, Zhangzhou (CN); Jinxiang Zeng, Zhangzhou (CN); Zhifei Fu, Shanghai (CN); Miaorong Luo, Shanghai (CN); Yang Zhang, Shanghai (CN); Jian Li, Shanghai (CN); Shuhui Chen, Shanghai (CN)

(73) Assignee: ZHANGZHOU PIEN TZE HUANG PHARMACEUTICAL CO., LTD., Fujian (CN)

( * ) Notice: Subject to any disclaimer, the term of this patent is extended or adjusted under 35 U.S.C. 154(b) by 0 days.

(21) Appl. No.: 17/633,293

(22) PCT Filed: Aug. 4, 2020

(86) PCT No.: PCT/CN2020/106895
§ 371 (c)(1),
(2) Date: Feb. 7, 2022

(87) PCT Pub. No.: WO2021/023193
PCT Pub. Date: Feb. 11, 2021

(65) Prior Publication Data
US 2022/0380350 A1 Dec. 1, 2022

(30) Foreign Application Priority Data

Aug. 8, 2019 (CN) .......................... 201910731662.9
Nov. 1, 2019 (CN) .......................... 201911059973.1

(51) Int. Cl.
C07D 403/14 (2006.01)
B01J 31/02 (2006.01)

(52) U.S. Cl.
CPC ........ *C07D 403/14* (2013.01); *B01J 31/0268* (2013.01)

(58) Field of Classification Search
CPC .................................................... C07D 403/14
USPC ....................................................... 544/357
See application file for complete search history.

(56) References Cited

U.S. PATENT DOCUMENTS

| 8,802,697 | B2 | 8/2014 | Bifulco, Jr. et al. |
| 9,434,700 | B2 | 9/2016 | Bifulco, Jr. et al. |
| 9,611,267 | B2 | 4/2017 | Wu et al. |
| 9,708,318 | B2 | 7/2017 | Lu et al. |
| 9,815,834 | B2 | 11/2017 | Verner et al. |
| 11,192,890 | B2 | 12/2021 | Patterson et al. |
| 2021/0040070 | A1 | 2/2021 | Zhang et al. |

FOREIGN PATENT DOCUMENTS

| CN | 104507943 A | 4/2015 |
| CN | 104540809 A | 4/2015 |
| CN | 105658642 A | 6/2016 |
| CN | 106459034 A | 2/2017 |
| CN | 107438607 A | 12/2017 |
| WO | WO-2009058076 A1 | 5/2009 |
| WO | WO-2018160076 A1 | 9/2018 |
| WO | WO-2018190326 A1 | 10/2018 |
| WO | WO-2018190349 A1 | 10/2018 |
| WO | WO-2019154364 A1 | 8/2019 |

OTHER PUBLICATIONS

Nov. 6, 2020 International Search Report issued in International Patent Application No. PCT/CN2020/106895.
Nov. 6, 2020 Written Opinion of the International Searching Authority issued in International Patent Application No. PCT/CN2020/106895.
Priority document—Chinese Patent Application CN2019107316629 (not published).
Priority document—Chinese Patent Application CN2019110599731 (not published).

*Primary Examiner* — Taofiq A Solola
(74) *Attorney, Agent, or Firm* — Harness, Dickey & Pierce, P.L.C.

(57) ABSTRACT

Provided are preparation methods for the chemical compound represented by formula (I) and an intermediate thereof.

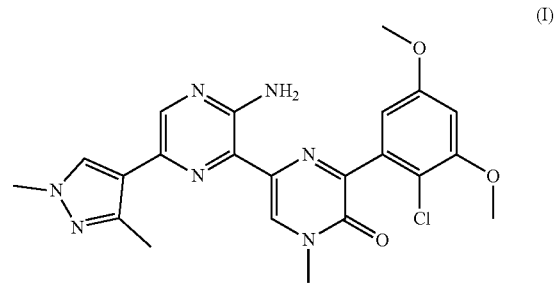

12 Claims, No Drawings

PYRAZINE-2(1H)-KETONE COMPOUND PREPARATION METHOD

CROSS-REFERENCE TO RELATED APPLICATIONS

This application is a U.S. National Phase Application under 35 U.S.C. 371 of International Application No. PCT/CN2020/106895, filed on Aug. 4, 2020, which claims the benefit of Chinese Patent Application No. 201910731662.9, filed on Aug. 8, 2019, and Chinese Patent Application No. 201911059973.1, filed on Nov. 1, 2019. The entire disclosures of the above applications are incorporated herein by reference.

TECHNICAL FIELD

The present disclosure relates to a preparation method of the compound of formula (I) and the intermediates thereof.

BACKGROUND

Fibroblast growth factor receptor (FGFR) is a receptor for fibroblast growth factor (FGF) signaling, which is a family consisting of four members (FGFR1, FGFR2, FGFR3, FGFR4) and a glycoprotein composed of extracellular immunoglobulin (Ig)-like domains, hydrophobic transmembrane domains and intracellular parts including tyrosine kinase domains. Fibroblast growth factor (FGF) plays an important role in many physiological regulation processes such as cell proliferation, cell differentiation, cell migration and angiogenesis through these receptors (FGFR). There are many evidences show that the abnormality of FGF signaling pathway (high expression, gene amplification, gene mutation, chromosome reorganization, etc.) is directly related to many pathological processes such as tumor cell proliferation, migration, invasion and angiogenesis. Therefore, FGFR has become an important therapeutic target, attracting extensive research and development interest.

CONTENT OF THE PRESENT INVENTION

The present disclosure provides a preparation method of compound of formula (I), which comprises the following reaction step:

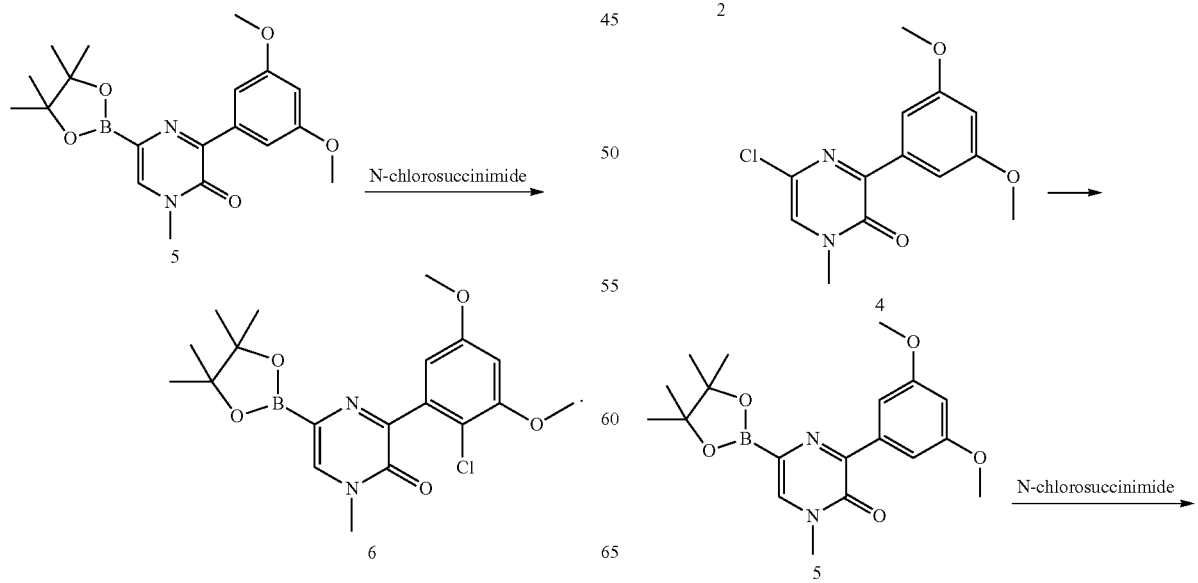

The present disclosure provides a method for preparing compound 6 with compound 5, wherein the reaction step is as follows:

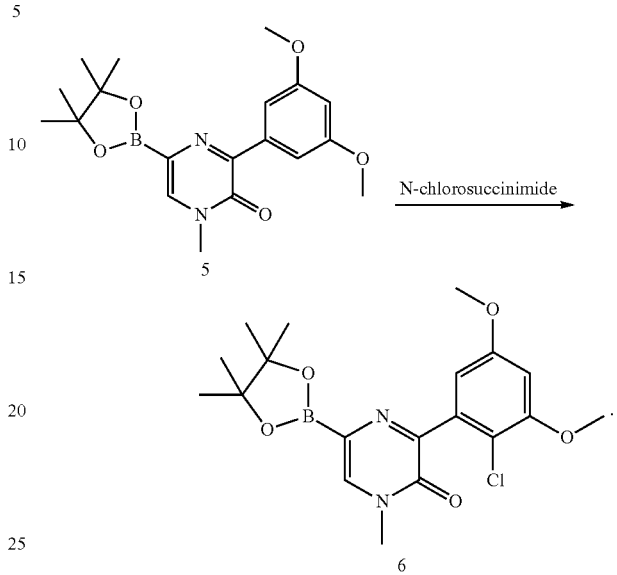

The present disclosure provides a method for preparing compound of formula (I) with compound 2, wherein the reaction steps are as follows:

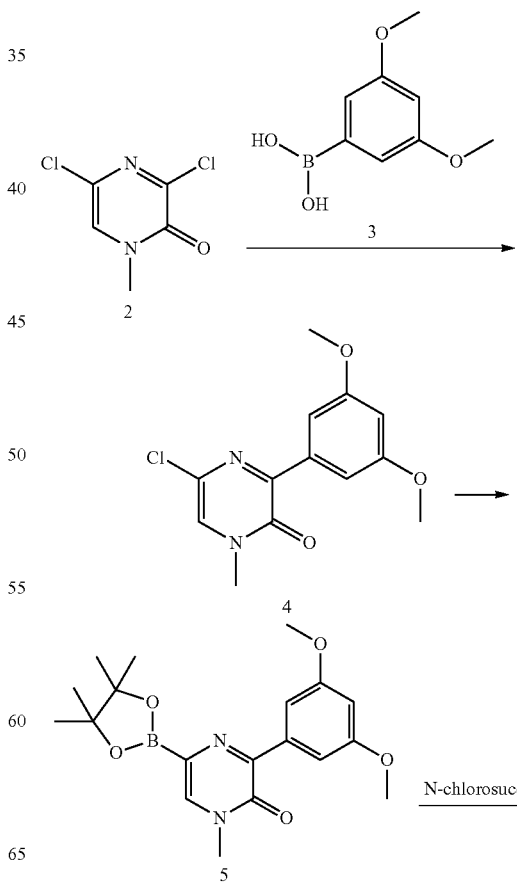

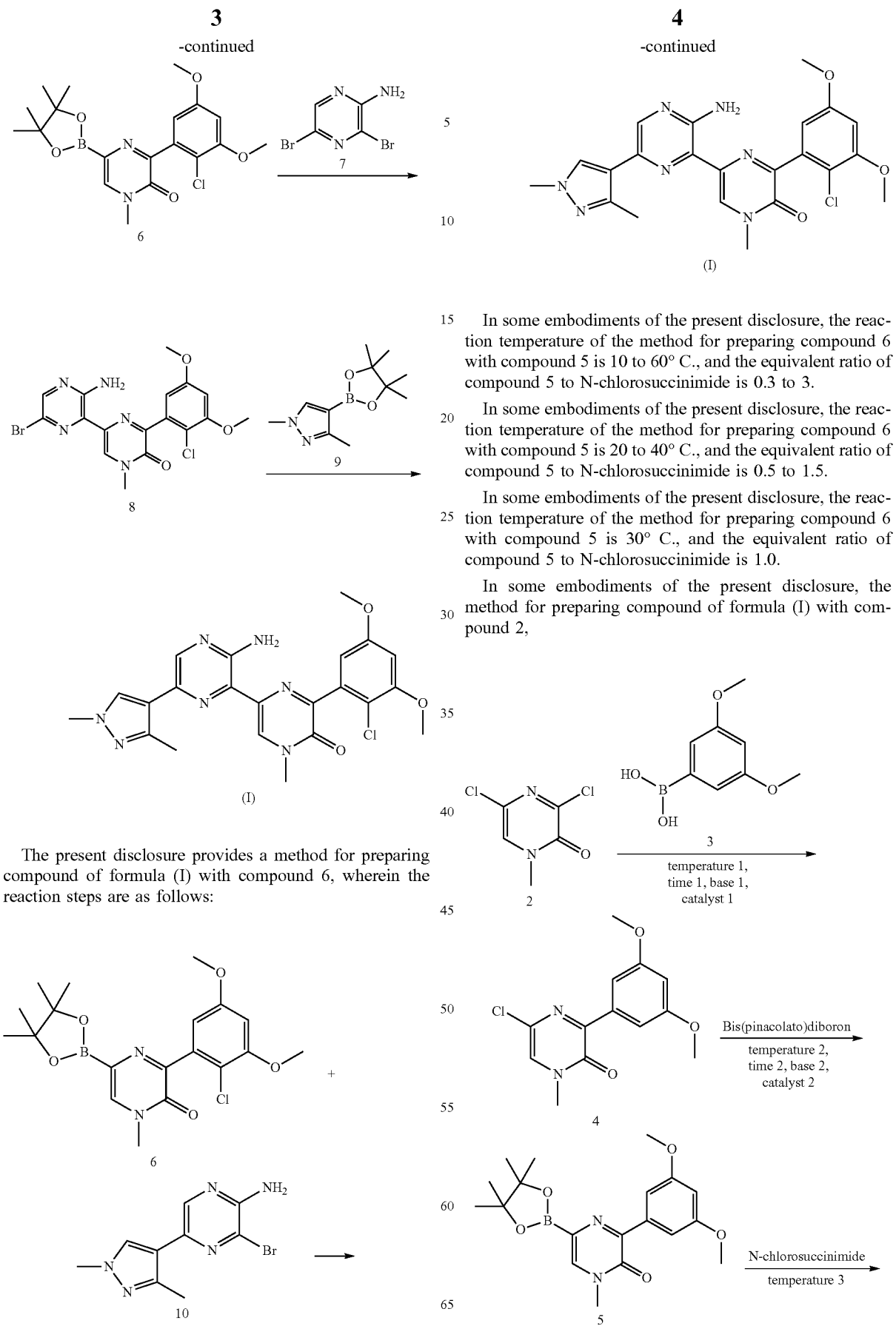

In some embodiments of the present disclosure, the reaction temperature of the method for preparing compound 6 with compound 5 is 10 to 60° C., and the equivalent ratio of compound 5 to N-chlorosuccinimide is 0.3 to 3.

In some embodiments of the present disclosure, the reaction temperature of the method for preparing compound 6 with compound 5 is 20 to 40° C., and the equivalent ratio of compound 5 to N-chlorosuccinimide is 0.5 to 1.5.

In some embodiments of the present disclosure, the reaction temperature of the method for preparing compound 6 with compound 5 is 30° C., and the equivalent ratio of compound 5 to N-chlorosuccinimide is 1.0.

In some embodiments of the present disclosure, the method for preparing compound of formula (I) with compound 2, The present disclosure provides a method for preparing compound of formula (I) with compound 6, wherein the reaction steps are as follows:

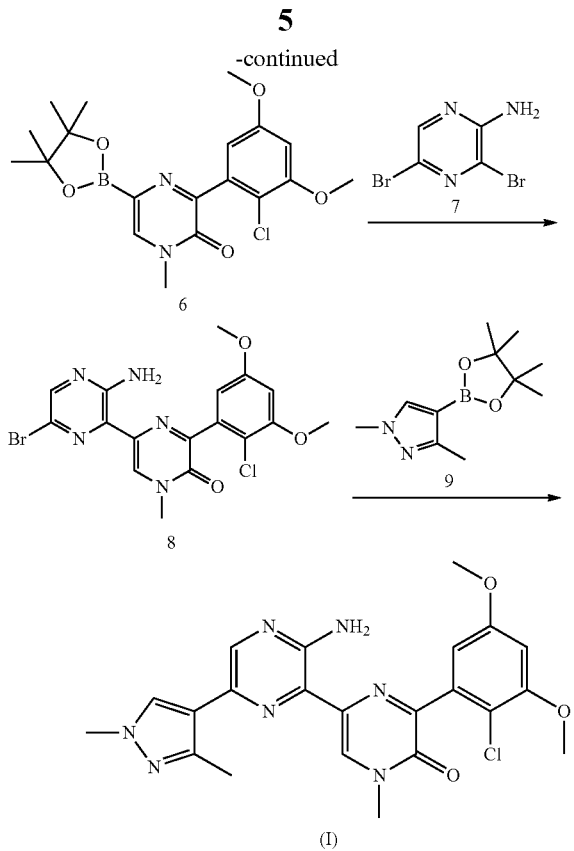

wherein,
temperature 1 is 70-110° C.;
time 1 is 2-20 hours:
base 1 is selected from the group consisting of sodium carbonate, potassium carbonate, palladium carbonate and potassium phosphate;
catalyst 1 is selected from the group consisting of tetrakis (triphenylphosphine) palladium, palladium acetate and Pd(dppf)Cl₂ and Pd₂dba₃;
the feeding ratio of compound 3 to compound 2 is 0.5-1.6;
temperature 2 is 80-120° C.;
time 2 is 2-24 hours:
base 2 is selected from the group consisting of sodium carbonate, potassium acetate, sodium acetate and potassium phosphate;
catalyst 2 is selected from the group consisting of tetrakis (triphenylphosphine) palladium, palladium acetate and Pd(dppf)Cl₂ and Pd₂dba₃;
the feeding ratio of bis(pinacolato)diboron to compound 4 is 0.7-3;
temperature 3 is 10-60° C.;
the feeding ratio of compound 5 to N-chlorosuccinimide is 0.3-3;
temperature 5 is 50-110° C.;
time 5 is 1-20 hours;
base 5 is selected from the group consisting of sodium carbonate, potassium carbonate, palladium carbonate and potassium phosphate;
catalyst 5 is selected from the group consisting of tetrakis (triphenylphosphine) palladium, palladium acetate and Pd(dppf)Cl₂ and Pd₂dba₃;
the feeding ratio of compound 7 to compound 6 is 0.6-1.8;
temperature 6 is 50-110° C.;
time 6 is 2-20 hours;
base 6 is selected from the group consisting of sodium carbonate, potassium carbonate, palladium carbonate and potassium phosphate;
catalyst 6 is selected from the group consisting of tetrakis (triphenylphosphine) palladium, palladium acetate and Pd(dppf)Cl₂ and Pd₂dba₃;
the feeding ratio of compound 9 to compound 8 is 0.6-1.8;
In some embodiments of the present disclosure, the method for preparing the compound of formula (I) with compound 2, wherein temperature 1 is 85-90° C.; time 1 is 4-10 hours; the feeding ratio of compound 3 to compound 2 is 0.7-1.3; temperature 2 is 85-100° C.; time 2 is 10-20 hours; the feeding ratio of bis(pinacolato)diboron to compound 4 is 1.5-2.5; temperature 3 is 20-40° C.; the feeding ratio of compound 5 to N-chlorosuccinimide is 0.5-1.5; temperature 5 is 50-70° C.; time 5 is 1-3 hours; the feeding ratio of compound 7 to compound 6 is 1.2-1.8; temperature 6 is 70-90° C.; time 6 is 14-18 hours; the feeding ratio of compound 9 to compound 8 is 1.2-1.6.

In some embodiments of the present disclosure, the method for preparing the compound of formula (I) with compound 2, wherein temperature 1 is 85° C.; time 1 is 6 hours; the feeding ratio of compound 3 to compound 2 is 0.7; temperature 2 is 95° C.; time 2 is 16 hours; the feeding ratio of bis(pinacolato)diboron to compound 4 is 2.0; temperature 3 is 30° C.; the feeding ratio of compound 5 to N-chlorosuccinimide is 1.0; temperature 5 is 60° C.; time 5 is 2 hours; the feeding ratio of compound 7 to compound 6 is 1.5; temperature 6 is 80° C.; time 6 is 16 hours; the feeding ratio of compound 9 to compound 8 is 1.4.

In some embodiments of the present disclosure, the method for preparing the compound of formula (I) with compound 6,

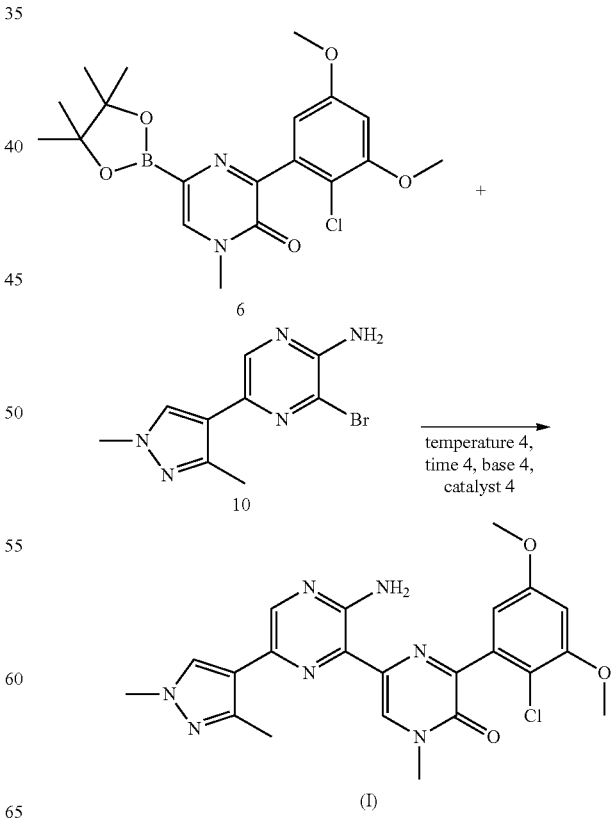

wherein, temperature 4 is 50-110° C.;

time 4 is 2-20 hours:

base 4 is selected from the group consisting of sodium carbonate, potassium carbonate, palladium carbonate and potassium phosphate;

catalyst 4 is selected from the group consisting of tetrakis (triphenylphosphine) palladium, palladium acetate and Pd(dppf)Cl$_2$ and Pd$_2$dba$_3$;

the feeding ratio of compound 10 to compound 6 is 0.6-1.8.

In some embodiments of the present disclosure, the method for preparing the compound of formula (I) with compound 6, wherein temperature 4 is 85-90° C.; time 4 is 4-10 hours; and the feeding ratio of compound 10 to compound 6 is 0.8-1.2.

In some embodiments of the present disclosure, the method for preparing the compound of formula (I) with compound 6, wherein temperature 4 is 100° C.; time 4 is 5 hours; and the feeding ratio of compound 10 to compound 6 is 1.0.

In the present disclosure, compound 6 is an intermediate for the preparation of the compound of formula (I).

Technical Effects

The trifluoroacetate of compound of formula (I) has a good inhibitory activity against wild-type FGFR, and relative high selectivity towards FGFR2 and FGFR3 compared to FGFR1 and FGFR4. The pharmacokinetic indexes of the trifluoroacetate of compound of formula (I) in mouse are good.

The process for synthesizing the compound of formula (I) and compound 6 provided by the present disclosure has the beneficial effects that the raw materials are cheap and easy to obtain and the disadvantages, such as strong corrosiveness and high toxicity of the reagents used, harsh reaction conditions, difficult separation and purification, and difficulty in industrialization etc, are overcomed.

specifically:

1) The raw materials of the method for preparing compound 6 of the present disclosure are conventional or common reagents, which are cheap and available in the market;

2) When preparing compound 6, the reaction conditions are mild and easy to control, and the post-processing is simple, the solid product is directly precipitated, and the product with high purity can be obtained by simple recrystallization, the yield is high, and the industrialization is easy to realize.

Definition and Description

Unless otherwise stated, the following terms and phrases used herein are intended to have the following meanings. A specific term or phrase should not be considered uncertain or unclear unless specifically defined, but should be understood in its ordinary meaning. When a trade name appears herein, it is intended to refer to the corresponding commodity or an active ingredient thereof.

The compounds of the present disclosure can be prepared by various synthetic methods well known to a person skilled in the art, including the specific embodiments listed below, the embodiments formed by the combination with other chemical synthesis methods, and equivalent alternative embodiments well known to a person skilled in the art, wherein the preferred embodiments include but are not limited to the examples of the present disclosure.

The chemical reactions of the embodiments of the present disclosure are carried out in a suitable solvent, and the solvent should be suitable for the chemical change, and the reagents and materials required therefor of the present disclosure. In order to obtain the compounds of the present disclosure, it is sometimes necessary for those skilled in the art to modify or select the synthetic steps or reaction schemes based on the existing embodiments.

The present disclosure will be specifically described below by way of embodiments, but the scope of the present disclosure is not limited thereto.

All solvents used in the present disclosure are commercially available and can be directly used without further purification.

The present disclosure uses the following abbreviations: eq stands for equivalent; DCM stands for dichloromethane; DMSO stands for dimethyl sulfoxide; MeOH stands for methanol; TFA stands for trifluoroacetic acid; Pd(dppf)Cl$_2$ stands for [1,1'-bis(diphenylphosphino)ferrocene]palladium dichloride; Pd$_2$dba$_3$ stands for tridibenzylideneacetone dipalladium.

The solvents used in the present disclosure are commercially available, and the commercially available compound adopts the supplier's catalog name. When the mixed solvent is added to the reaction solution, the solvents can be mixed first and then added to the reaction solution; or each single solvent can be added to the reaction solution in sequence and mixed in the reaction system.

Compounds are named according to conventional naming principles in the field or using ChemDraw® software, and commercially available compounds are named using supplier catalog names.

DETAILED DESCRIPTION OF THE PREFERRED EMBODIMENT

The present disclosure will be specifically described below by way of embodiments carried out, but the scope of the present disclosure is not limited thereto. The present disclosure has been described in detail herein, wherein specific embodiments thereof are also disclosed, for those skilled in the art, it is obvious that various changes and improvements can be made to the specific embodiments of the present disclosure without departing from the spirit and scope of the present disclosure.

Example 1: Synthesis of the Compound of Formula (I)

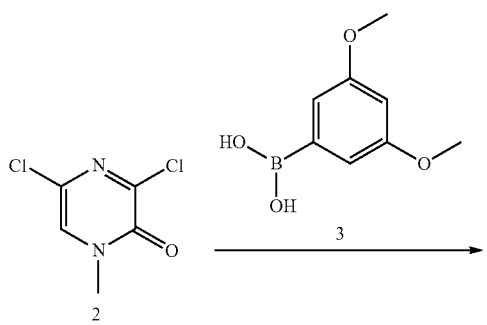

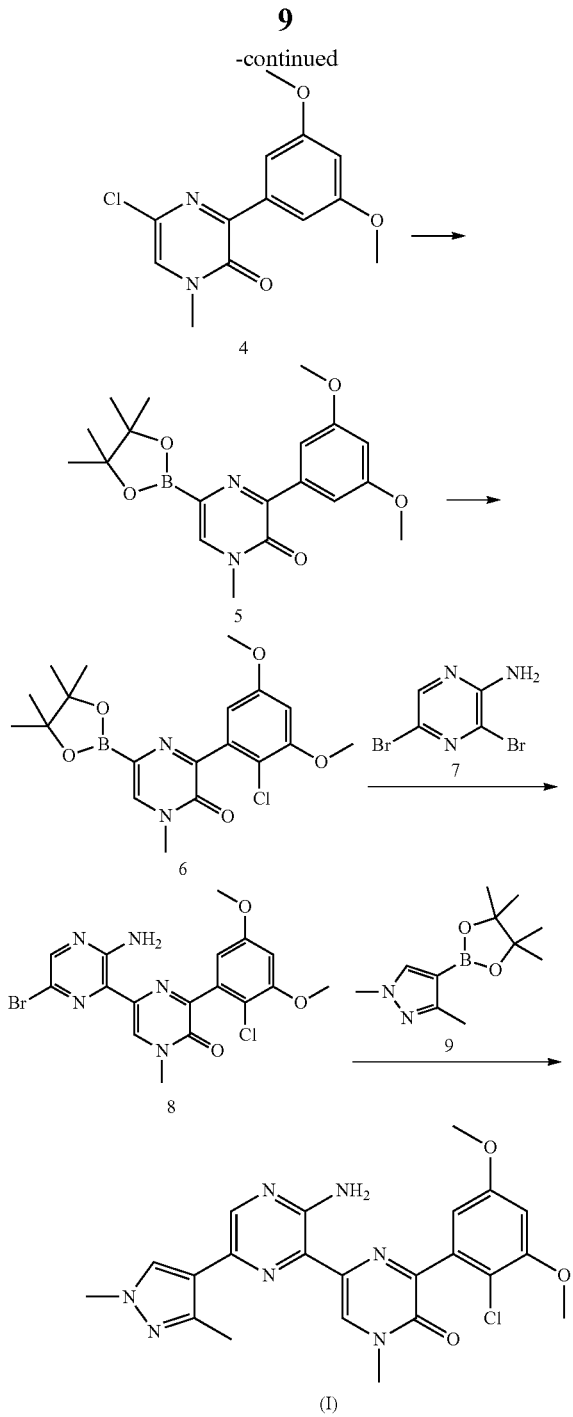

Step 1: Synthesis of Compound 4

1,4-Dioxane (14.82 L), compound 2 (3.0 kg, 16.77 mol) were added to a 50 L reaction kettle, followed by addition water (8.72 L) and compound 3 (2.18 kg, 11.98 mol). The reaction solution was purged with nitrogen for 30 minutes, then sodium carbonate (1.9 kg, 17.97 mol), tetrakis (triphenylphosphine) palladium (277 g, 0.24 mol) were added, the air in the reaction system was replaced 3 times with nitrogen, and the reaction solution was heated to 85° C. for 6 hours. The reaction solution was cooled down, 20.9 L of water was added, and the reaction solution was cooled to room temperature and filtered. The filter cake was washed with water, and rinsed with petroleum ether:ethyl acetate=2:1 (4.5 L×2). Then the filter cake was dried to obtain a yellow solid, which is compound 4 (3.39 kg).

Step 2: Synthesis of Compound 5

1,4-Dioxane (17.6 L) was added to a 50 L reaction kettle, followed by addition of compound 4 (2.35 kg, 8.37 mol), bis(pinacolato)diboron (3.19 kg, 12.56 mol), potassium acetate (1.64 kg, 16.74 mol), tricyclohexylphosphine (140.9 g, 0.50 mol) and $Pd_2(dba)_3$ (153.3 g, 0.167 mol). The air in the reaction system was replaced 3 times with nitrogen and the reaction solution was heated to 95° C. and reacted for 16 hours. The reaction solution was cooled to room temperature and filtered. The filter cake was rinsed with petroleum ether. Dichloromethane (17.6 L) and water (11.5 L) were added to the filter cake, and allowed to stand still for layer separation. The organic phase was washed with water, dried with sodium sulfate and filtered with diatomite. The filtrate was concentrated under reduced pressure, the crude product was slurried with petroleum ether:ethyl acetate=1:1. Then the crude product was filtered, the filter cake was rinsed with petroleum ether:ethyl acetate=2:1 (1.5 L), and dried to obtain a gray solid, which is compound 5 (2.37 kg).

Step 3: Synthesis of Compound 6

25.1 L of acetonitrile was added to a 50 L jacketed reaction kettle, followed by addition of compound 5 (2501.21 g) with stirring. The yellow suspension was heated to 30° C., then aluminum trichloride (90.31 g) and N-chlorosuccinimide (861.22 g) were added in sequence, and the reaction was continued for 14 hours at 30° C. Next, 85.51 g of sodium sulfite was added, and the reaction solution was stirred for 10 minutes. 5.1 L of dichloromethane was then added, and the mixture was stirred for 0.5 hours. The reaction solution was filtered with diatomite. The filter cake was rinsed with 0.5 L×2 DCM, and the filtrate was collected. 5 L of DCM was added into the jacketed reaction kettle, then the concentrated solid crude product was transferred to the reaction kettle, 15.5 L of n-heptane was added slowly, the reaction solution was stirred at 20-30° C. for 1 hour, and then filtered. The filter cake was washed with DCM/n-heptane (v/v=1/3) 0.5 L×2, the filter cake was collected and dried at 45-50° C. to obtain compound 6 as a solid (1750.41 g, light yellow solid).

Step 4: Synthesis of Compound 8

10.5 L of 1,4-dioxane and 2.65 L of water were added to a jacketed reaction kettle, and then stirring was started. Compound 6 (1750.41 g), compound 7 (1630.91 g) and potassium carbonate 894.52 g were added to the 50 L jacketed reaction kettle. The yellow suspension was formed and the air in the reaction system was replaced twice with nitrogen. 99.67 g of tetrakis (triphenylphosphine) palladium was added to the reaction system under nitrogen flow, the temperature was raised to 60° C., and the reaction was continued for 2 hours under nitrogen atmosphere. 7.9 L of water was added to the reaction system, a solid was precipitated, and the reaction solution was stirred for 1 hour, and then cooled to room temperature. After cooling, a tabletop suction filtration funnel was used for suction filtration, and the filter cake was rinsed with 1 L×2 of water. 7.1 L of ethanol/ethyl acetate (1/1) was added into a 50 L jacketed reaction kettle, and the filter cake was then transferred to the 50 L jacketed reaction kettle with stirring. The reaction solution was heated to 60° C. with stirring for 1 to 2 hours, then the reaction solution was cooled to room temperature, and a tabletop suction filter funnel was used for suction filtration. The filter cake was rinsed with ethanol/ethyl acetate (1/1) 0.5 L×2, and dried to obtain compound 8 as a solid (1441.42 g, yellow solid).

Step 5: Synthesis of the Compound of Formula (I)

11.6 L of 1,4-dioxane and 2.9 L of water were added into a jacketed reaction kettle, followed by addition of compound 8 (1440.21 g), compound 9 (989.81 g) and potassium carbonate 659.55 g were added to the jacketed reaction kettle with stirring. The air in the reaction system was replaced twice with nitrogen, and 73.58 g of tetrakis(triphenylphosphine)palladium was added to the reaction system under nitrogen flow. The temperature was raised to 80° C., and the reaction was continued for 16 hours under nitrogen atmosphere. 17.8 L of water was added to the reaction system, a solid was precipitated, and the reaction solution was stirred for 1 hour, and then cooled to room temperature. After cooling, the reaction solution was subjected to suction filtration, and the filter cake was rinsed with 3 L×2 water. 7.3 L of ethanol/deionized water (1/1) was added into a 50 L jacketed reaction kettle, and the filter cake was transferred to the 50 L jacketed reaction kettle with stirring. The reaction solution was heated to 60° C. with stirring for 1 hour, and then cooled to room temperature, followed by suction filtration. The filter cake was rinsed with 3 L×2 ethanol, and dried to obtain the compound of formula (I) as a solid (1167.21 g). $^1$H NMR (400 MHz, CDCl$_3$) δ: 8.51 (s, 1H), 8.15 (s, 1H), 6.71 (d, J=2.8 Hz, 1H), 6.63 (d, J=2.8 Hz, 1H), 6.43 (brs, 2H), 3.94 (s, 3H), 3.92 (s, 3H), 3.84 (s, 3H), 3.79 (s, 3H), 2.55 (s, 3H).

Example 2: Preparation of the Compound of Formula (I)

5 eq) were added to 1,4-dioxane (50 mL) and water (13 mL). The air in the reaction system was replaced with nitrogen, and the reaction solution was heated to 100° C. and stirred under reflux for 5 hours under nitrogen atmosphere. Most of the solution was concentrated under reduced pressure, diluted with ethyl acetate (200 mL), and washed twice with water (100 mL, 100 mL) and once more with saturated sodium chloride solution (200 mL). The organic phase was dried with anhydrous sodium sulfate, then filtered and concentrated under reduced pressure. The obtained crude product was dissolved in DMSO (30 mL), the insoluble substance was filtered out, and the result was separated and purified by high performance liquid chromatography (column: Boston Green ODS 150×30 mm 5 μm; mobile phase: [water (0.1% TFA)-ACN]; B %: 40%-48%, 9 min) to obtain the trifluoroacetate of the compound of formula (I) (500 mg, 1.06 mmol, yield: 49.50%). The salt was dissolved in dichloromethane, and washed with saturated sodium carbonate. The organic phase is dried with anhydrous sodium sulfate, filtered, and the filtrate was spin-dried to obtain the compound of formula (I). $^1$H NMR (400 MHz, CDCl$_3$) δ: 8.51 (s, 1H), 8.15 (s, 1H), 6.71 (d, J=2.8 Hz, 1H), 6.63 (d, J=2.8 Hz, 1H), 6.43 (brs, 2H), 3.94 (s, 3H), 3.92 (s, 3H), 3.84 (s, 3H), 3.79 (s, 3H), 2.55 (s, 3H).

Example 3: Preparation of the Trifluoroacetate of the Compound of Formula (I)

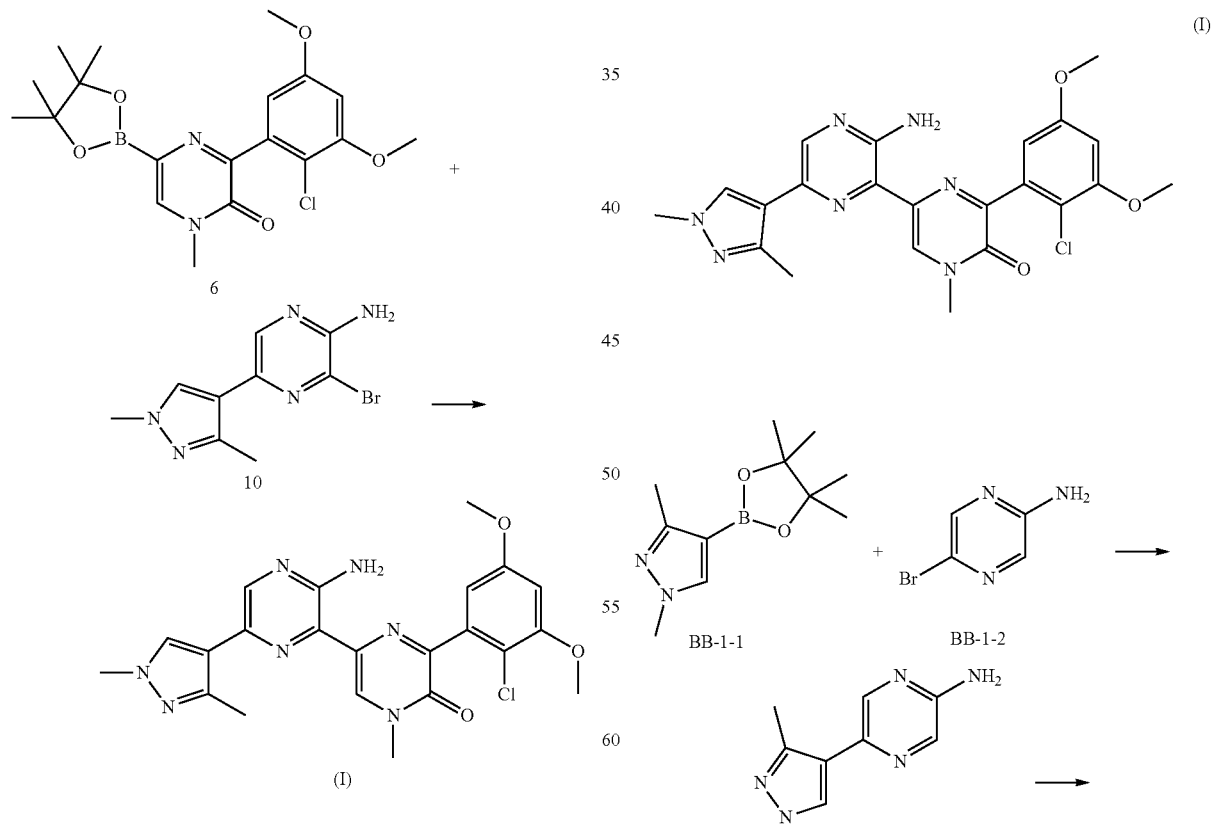

In a 100 mL single-neck flask, compound 6 (1.64 g, 4.03 mmol, 1 eq), compound 10 (1.08 g, 4.03 mmol, 1 eq), tetrakis(triphenylphosphine)palladium (466.01 mg, 403.28 umol, 0.1 eq) and potassium carbonate (2.79 g, 20.16 mmol, -continued

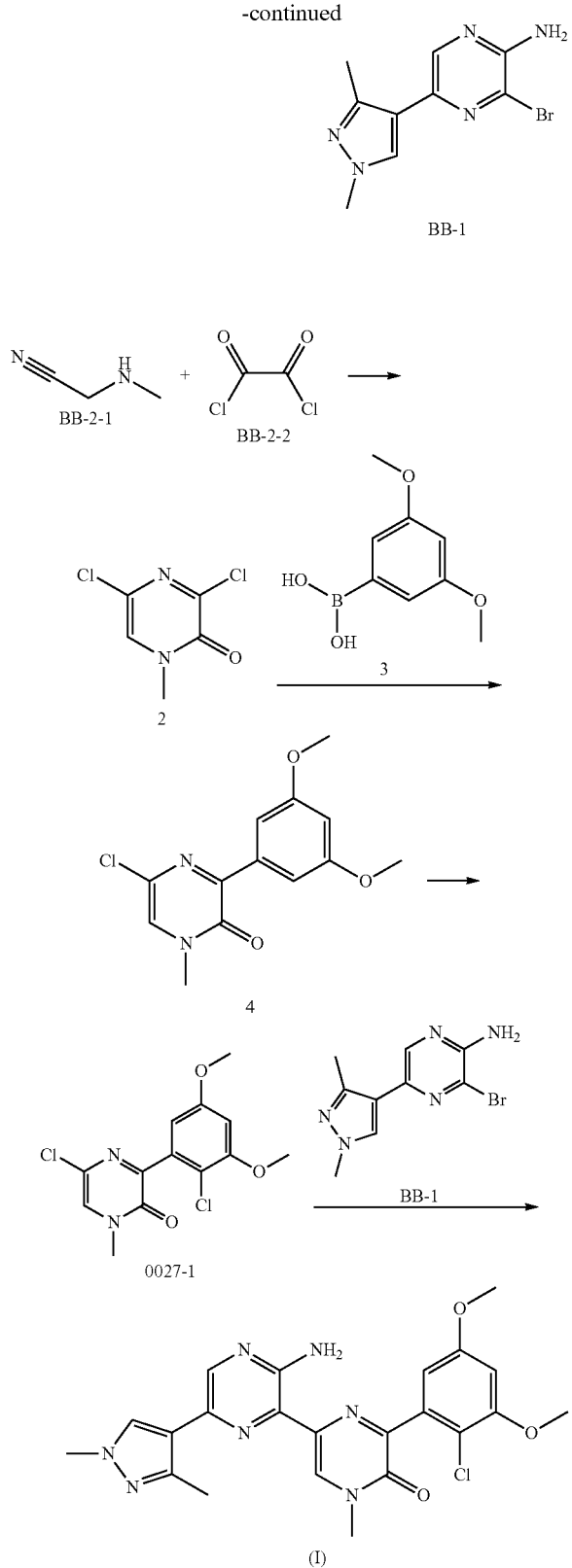

Step 1: Synthesis of Compound BB-1-3

Compound BB-1-2 (2.0 g, 11.49 mmol, 1 eq) and compound BB-1-1 (2.6 g, 11.49 mmol, 1 eq) were dissolved in water (6.0 mL) and dioxane (25.0 mL), then [1,1'-bis(diphenylphosphino)ferrocene] palladium dichloride (841 mg, 1.15 mmol, 0.1 eq) and potassium carbonate (4.8 g, 34.48 mmol, 3 eq) were added, the reaction solution was heated to 100° C. and reacted for 16 hours under the protection of nitrogen. The resulting reaction solution was subjected to suction filtration and rotary evaporation, and the crude product was purified by column chromatography (petroleum ether:ethyl acetate=1:0-0:1) to obtain compound BB-1-3.

MS (ESI) m/z: 190.0 [M+H]$^+$.

Step 2: Synthesis of Compound BB-1

Compound BB-1-3 (0.5 g, 2.64 mmol, 1 eq) and pyridine (209 mg, 2.64 mmol, 213.28 µL, 1 eq) were added to chloroform (20.0 mL), cooled to 0° C. and then bromine (422 mg, 2.64 mmol, 136.22 µL, 1 eq) was added. The reaction solution was reacted for 18 hours at room temperature of 28° C. The reaction was quenched with sodium thiosulfate (1.0 mL), then subjected to suction filtration, the filtrate was concentrated. The crude product was purified by flash silica gel column chromatography (petroleum ether: ethyl acetate=1:0-1:1) to obtain Compound BB-1. MS (ESI) m/z: 267.9 [M+H]$^+$.

$^1$H NMR (400 MHz, CD$_3$OD) δ: 8.12 (s, 1H) 7.90 (s, 1H) 3.86 (s, 3H) 2.43 (s, 3H).

Step 3: Synthesis of Compound 2

Under the protection of nitrogen, compound BB-2-1 (2.0 g, 18.77 mmol, 2.17 mL, 1 eq, HCl) was dissolved in chlorobenzene (15.0 mL), and compound BB-2-2 (8.3 g, 65.69 mmol, 5.8 mL, 3.5 eq) was added dropwise at 25° C., the mixture was slowly heated to 90° C. and stirred for 16 hours. Water (30.0 mL) and ethyl acetate (30.0 mL) were added to the reaction system, and allowed to stand still for layer separation. At the same time, the aqueous phase was extracted three times with ethyl acetate (20.0 mL, 20.0 mL, 20.0 mL). The organic phases were combined, washed once with saturated sodium chloride solution (30.0 mL), and finally dried with anhydrous sodium sulfate, filtered and concentrated under reduced pressure. The crude product was separated and purified by column chromatography (petroleum ether:ethyl acetate=1:0-2:1) to obtain compound 2. MS (ESI) m/z: 178.7 [M+1]$^+$.

$^1$H NMR (400 MHz, CDCl$_3$) δ: 7.26 (s, 1H), 3.61 (s, 3H).

Step 4: Synthesis of Compound 4

In a microwave tube, under the protection of nitrogen, compound 2 (0.2 g, 1.12 mmol, 1 eq) and compound 3 (213 mg, 1.17 mmol, 1.05 eq) were dissolved in the mixed solution of dioxane (1.5 mL) and water (1.5 mL), palladium tetrakistriphenylphosphorus (65 mg, 55.86 µmol, 0.05 eq) and sodium carbonate (130 mg, 1.23 mmol, 1.1 eq) were added, and the mixture was stirred in microwave at 120° C. for 30 minutes. The reaction solution was concentrated directly. The crude product was separated by column chromatography (petroleum ether:ethyl acetate=1:0-0:1) (TLC detection, petroleum ether:ethyl acetate=1:1) to obtain compound 4. MS (ESI) m/z: 281.0 [M+1]$^+$.

$^1$H NMR (400 MHz, CDCl$_3$) δ: 7.64 (d, 2H), 7.28 (s, 1H), 6.59 (t, 1H), 3.86 (s, 6H), 3.61 (s, 3H).

Step 5: Synthesis of Compound 0027-1

Under the protection of nitrogen, compound 4 (250 mg, 890.61 µmol, 1 eq) was dissolved in a mixed solvent of acetonitrile (20.0 mL) and dichloromethane (5.0 mL), and then sulfonyl chloride (84 mg, 623.43 µmol, 62.33 µL, 0.7 eq) in acetonitrile (2.5 mL) was added dropwise slowly at 0° C. The mixture was stirred at 0° C. for 10 minutes. The reaction was quenched by adding methanol (5.0 mL) to the reaction solution, and the reaction solution was concentrated to dryness under reduced pressure. The crude product was separated by column chromatography (petroleum ether:ethyl acetate=1:0-0:1) (TLC detection, petroleum ether:ethyl acetate=1:1) to obtain compound 0027-1. MS (ESI) m/z: 314.9 [M+H]$^+$.

Step 6: Synthesis of the Compound of Formula (I)

In a three-necked flask, compound 0027-1 (59 mg, 186.49 μmol, 1 eq), bis(pinacolato)diboron (52 mg, 205.14 μmol, 1.1 eq), palladium acetate (5 mg, 20.51 μmol, 0.11 eq) and 2-dicyclohexylphosphorus-2,4,6-triisopropylbiphenyl (20 mg, 41.03 μmol, 0.22 eq), potassium acetate (60 mg, 615.42 μmol, 3.3 eq) were added to dioxane (4.0 mL) solution. The air in the reaction system was replaced with nitrogen, and under the saturation of nitrogen, the reaction solution was heated up to 100° C., refluxed and stirred for 30 minutes, then cooled to 25° C. Compound BB-1 (50 mg, 186.49 μmol, 1 eq), dichloromethane complex of [1,1'-bis(diphenylphosphino)ferrocene] palladium dichloride (15 mg, 18.65 μmol, 0.1 eq), potassium carbonate (77 mg, 559.47 μmol, 3 eq), dioxane (4.0 mL) and water (2.0 mL) were added. The air in the reaction system was replaced with nitrogen, and under the saturation of nitrogen, the reaction solution was heated to 100° C., refluxed and stirred for 8 hours. The reaction solution was concentrated directly. The obtained crude product was separated and purified by high performance liquid chromatography (chromatographic column: Boston Green ODS150×30 mm 5 μm; Mobile phase: [Water (0.1% TFA)-ACN]; B %: 30%-60%, 8 min) to obtain the trifluoroacetate of the compound of formula (I). MS (ESI) m/z: 468.2 [M+H]$^+$. $^1$H NMR (400 MHz, CD$_3$OD) δ: 8.79 (s, 1H), 8.09 (m, 2H), 6.76 (m, 2H), 3.93 (s, 3H), 3.89 (s, 3H), 3.84 (s, 3H), 3.80 (s, 3H), 2.54 (s, 3H).

Experimental Example 1: Evaluation of Inhibitory Activity of Wild-Type Kinase In Vitro The IC$_{50}$ value was determined using $^{33}$P isotope-labeled kinase activity test (Reaction Biology Corp) to evaluate the inhibitory ability of the compounds to be tested on human FGFR4 and VEGFR2.

Buffer conditions: 20 mM 4-(2-hydroxyethyl)-1-piperazineethanesulfonic acid (Hepes) (pH 7.5), 10 mM MgCl$_2$, 1 mM ethylene glycol-bis-(2-aminoethyl ether)tetra acetic acid (EGTA), 0.02% polyoxyethylene lauryl ether (Brij35), 0.02 mg/ml bovine serum albumin (BSA), 0.1 mM sodium vanadate (Na$_3$VO$_4$), 2 mM dithiothreitol (DTT), 1% DMSO.

Experimental steps: At room temperature, the compounds to be tested were dissolved in DMSO to prepare a 10 mM solution for use. The substrate was dissolved in the freshly prepared buffer, and the kinase to be tested was added thereto and mixed well. The DMSO solution in which the compounds to be tested were dissolved was added to the above-mentioned homogeneous reaction solution using acoustic technology (Echo 550). The compound concentration in the reaction solution is 10 μM, 3.33 μM, 1.11 μM, 0.370 μM, 0.123 μM, 41.2 nM, 13.7 nM, 4.57 nM, 1.52 nM, 0.508 nM, or 10 μM, 2.50 μM, 0.62 μM, 0.156 μM, 39.1 nM, 9.8 nM, 2.4 nM, 0.61 nM, 0.15 nM, 0.038 nM. After incubating for 15 minutes, to the reaction solution was added $^{33}$P-ATP (activity: 0.01 μCi/μL, with corresponding concentration listed in Table 1) to start the reaction. The supplier product number, batch number, and concentration information in the reaction solution of FGFR1, FGFR4 and substrate thereof are listed in Table 1. After incubating the kinase reaction for 120 minutes at room temperature, the reaction solution was spotted on P81 ion exchange filter paper (Whatman #3698-915). After the filter paper was repeatedly washed with 0.75% phosphoric acid solution, the radioactivity of the phosphorylated substrate remaining on the filter paper was measured. The kinase activity data was expressed by comparing the kinase activity of the groups containing the compounds to be tested with that of the blank group (containing only DMSO). The IC$_{50}$ value was obtained by curve fitting using Prism4 software (GraphPad), and the experimental results were shown in Table 2.

TABLE 1

Related information about kinases, substrates and ATP in in-vitro tests

| Kinase | Supplier | Cat # | Lot # | ATP concentration (uM) |
|---|---|---|---|---|
| FGFR1 | Invitrogen | PV3146 | 28427Q | 5 |
| FGFR2 | Invitrogen | PV3368 | 315171 | 5 |
| FGFR3 | Invitrogen | PV3145 | 28459R | 30 |
| FGFR4 | Invitrogen | P3054 | 26967J | 2.5 |

| Substrate | | | | Substrate concentration in reaction solution (M) |
|---|---|---|---|---|
| pEY (mg/ml) + Mn | Sigma | P7244-250MG | 062K5104V | 0.2 |
| pEY (mg/ml) + Mn | Sigma | P7244-250MG | 062K5104V | 0.2 |
| pEY (mg/ml) + Mn | Sigma | P7244-250MG | 062K5104V | 0.2 |
| pEY (mg/ml) + Mn | Sigma | P7244-250MG | 062K5104V | 0.2 |

TABLE 2

In vitro screening test results of the compounds of the present disclosure

| | IC$_{50}$ (nM) | | | | Selectivity | |
|---|---|---|---|---|---|---|
| Compound | FGFR1 | FGFR2 | FGFR3 | FGFR4 | FGFR1/ 2 | FGFR1/ 3 |
| Trifluoroacetate of compound of formula (I) | 2.12 | 0.53 | 0.69 | 106 | 4.02 | 3.06 |

Conclusion: The trifluoroacetate of compound of formula (I) has a good inhibitory activity against wild-type FGFR, and relative high selectivity towards FGFR2 and FGFR3 compared to FGFR1 and FGFR4.

Experimental Example 2: Evaluation of Pharmacokinetic of Compound

Experimental purpose: To test the pharmacokinetics of the compound in mice

Experimental Materials:

CD-1 mouse (male), vehicle (0.5% (w/v) methylcellulose 0.5% (v/v) Tween 80 aqueous solution), trifluoroacetate of compound 0027.

1. Formulation of Preparations for Administration:

The vehicle was an aqueous solution of 0.5% (w/v) methylcellulose and 0.5% (v/v) Tween 80, and it was prepared according to the following procedure:

a. About 50% volume of purified water was added to a suitable container and heated to about 60° C. to 70° C.

b. When the water temperature reached the specified value range, the heater was turned off. The required amount of methylcellulose was added slowly to the above container with constant stirring.

c. The mixture was stirred continuously at 4° C. until a clear solution was obtained visually.

d. The required volume of Tween 80 was added to the above solution. The mixture was stirred continuously until Tween 80 became being evenly dispersed and a clear solution was obtained visually.

e. The above solution was diluted to the final volume using an appropriate amount of pure water.

f. Continue stirring until a homogeneous solution was formed.

Formulation of Preparations for Intragastric Administration:

a. An appropriate amount of the test product was weighed and put into a glass bottle;

b. 70% volume of vehicle (0.5% (w/v) methyl cellulose 0.5% (v/v) Tween 80 aqueous solution) was added;

c. The preparation was stirred until it was visually homogeneous, and subjected to ultrasound in water bath as needed;

e. Make up the remaining volume of 0.5% methylcellulose+0.5% Tween 80, and the mixture was stirred until being visually homogeneous.

2. Administration

Animals in groups 1 and 2 were administrated 5 mg/mL and 30 mg/mL compounds by single gavage, with a dose volume of 10 mL/kg.

The body weight of the animals was weighed before administration, and the administration volume was calculated based on the body weight.

3. Sample Collection and Processing

Whole blood samples (30 μL) were collected at the prescribed time (0.25, 0.5, 1, 2, 4, 6, 8, 24 h) through saphenous vein blood collection, and the actual blood collection time was recorded in the test record. The acceptable error of the collection time point was a time point within 1 hour of the administration ±1 minute, and the acceptable error of other time points is a theoretical time ±5%.

All blood samples were immediately transferred to labeled commercial centrifuge tubes containing K2-EDTA. After being collected, the blood samples were centrifuged at 3200 rpm for 10 minutes at 4° C. to aspirate the supernatant plasma, which was quickly placed in dry ice, kept at −20° C. or a lower temperature for LC-MS/MS analysis. The pharmacokinetic parameters were calculated.

The experimental results are shown in Table 3.

TABLE 3

| Pharmacokinetic test results | | |
|---|---|---|
| Compound | Trifluoroacetate of compound of formula (I) | |
| Parameters\Dosage | 50 mpk | 300 mpk |
| $C_{max}$ (nM) | 14800 | 42100 |
| $T_{max}$ (hr) | 1.00 | 7.00 |
| $T_{1/2}$ (hr) | 2.46 | ND |
| $T_{last}$ (hr) | ND | 24.0 |
| $AUC_{0-last}$ (nM.hr) | 85826 | 699413 |
| $AUC_{0-inf}$ (nM.hr) | 95847 | ND |
| $MRT_{0-last}$ (h) | 4.33 | 11.1 |
| $MRT_{0-inf}$ (h) | 5.39 | ND |

ND stands for: Not determined.

Conclusion: The trifluoroacetate of the compound of formula (I) has good pharmacokinetic indexes in mice.

What is claimed is:

1. A method for preparing compound 6 with compound 5, wherein the reaction step is as follows:

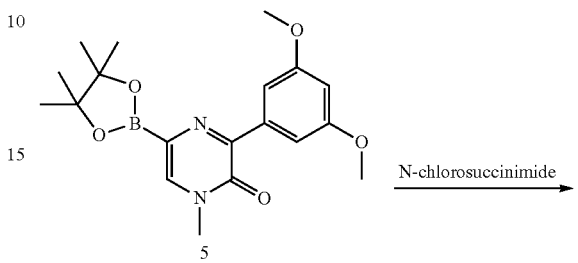

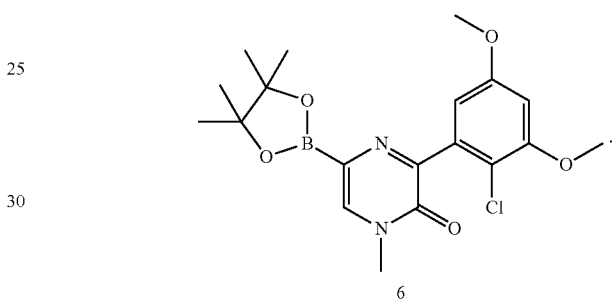

2. A method for preparing compound of formula (I) with compound 2, wherein the reaction steps are as follows:

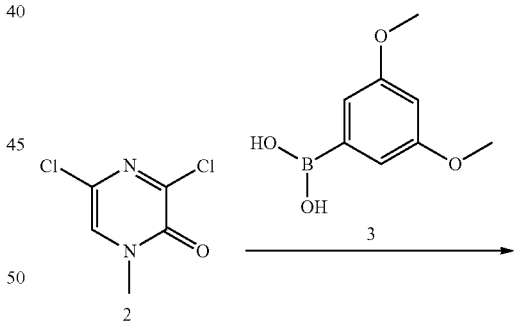

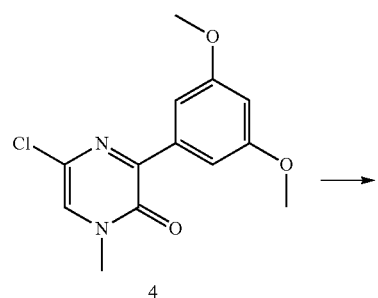

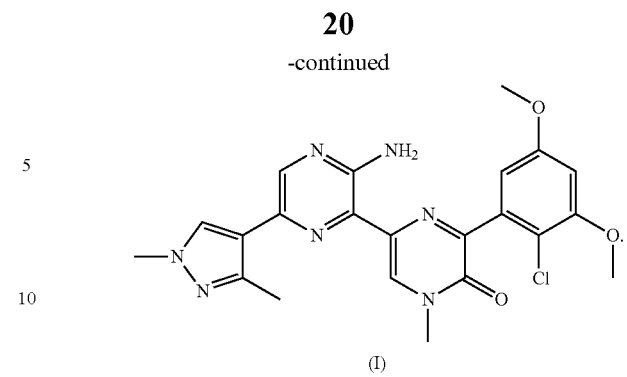

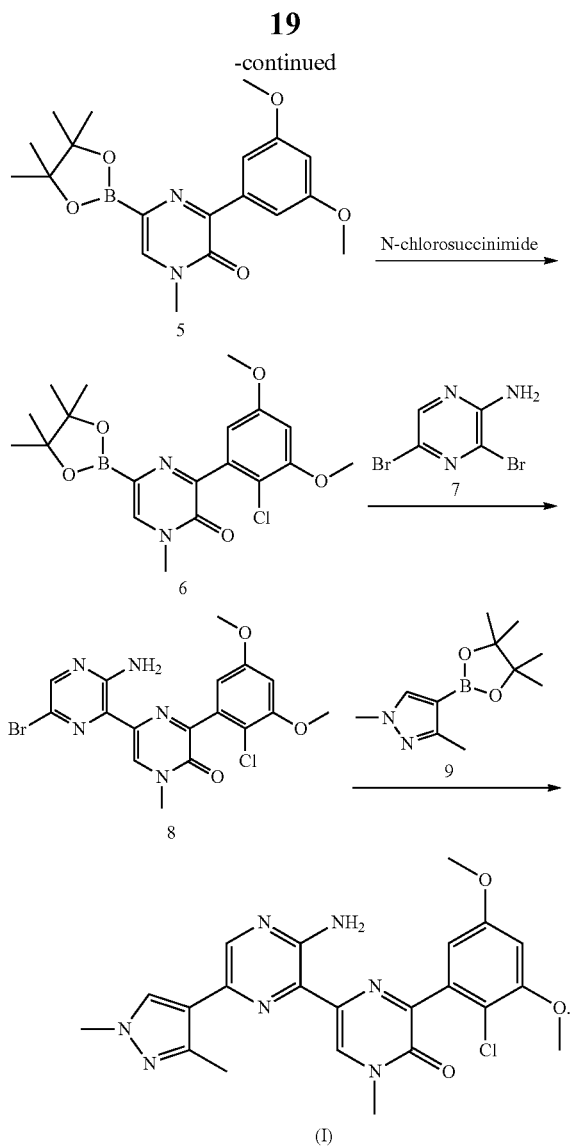

3. A method for preparing compound of formula (I) with compound 6, wherein the reaction step is as follows:

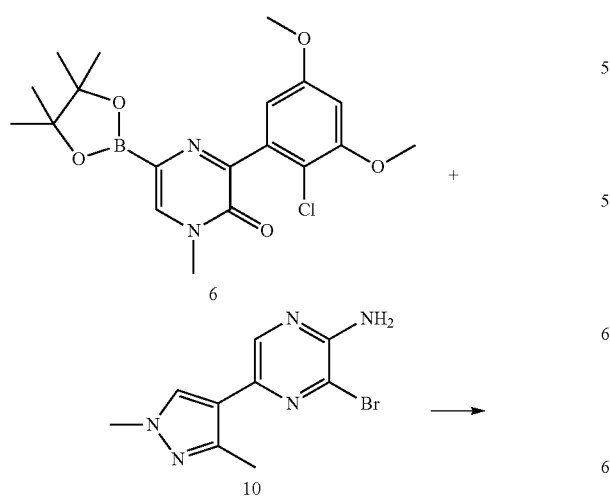

4. The method according to claim 1, wherein the reaction temperature is 10 to 60° C., and the equivalent ratio of compound 5 to N-chlorosuccinimide is 0.3 to 3.

5. The method according to claim 4, wherein the reaction temperature is 20 to 40° C., and the equivalent ratio of compound 5 to N-chlorosuccinimide is 0.5 to 1.5.

6. The method according to claim 5, wherein the reaction temperature is 30° C., and the equivalent ratio of compound 5 to N-chlorosuccinimide is 1.0.

7. The method according to claim 2:

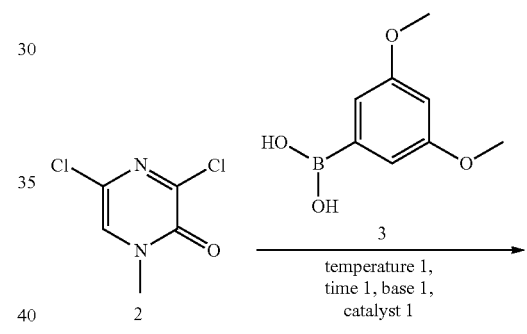

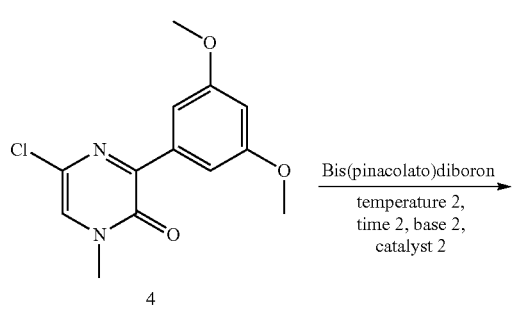

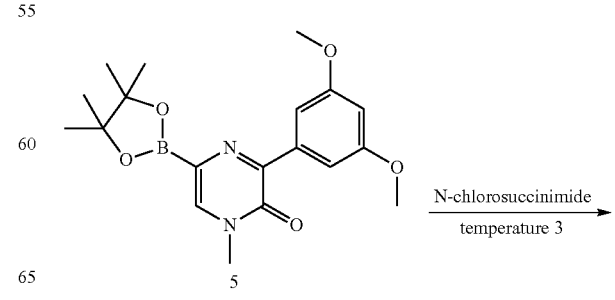

-continued

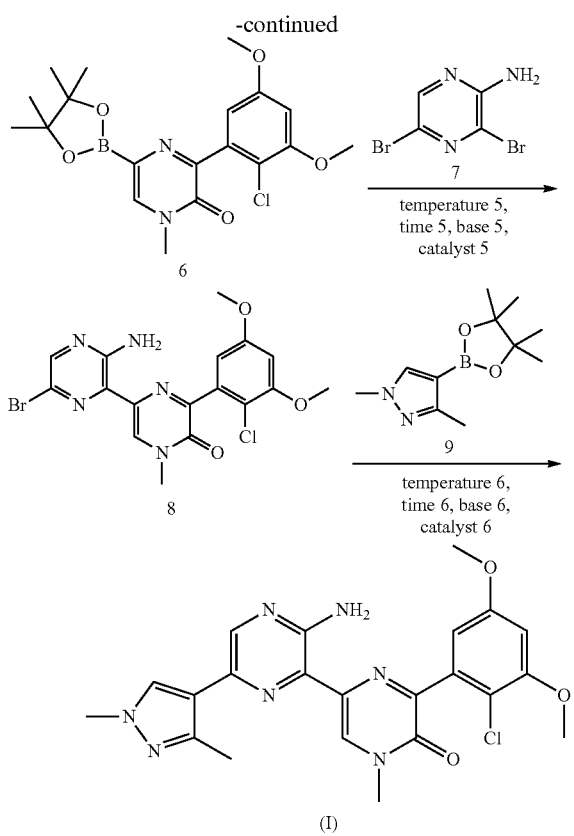

wherein,
temperature 1 is 70-110° C.;
time 1 is 2-20 hours;
base 1 is selected from the group consisting of sodium carbonate, potassium carbonate, palladium carbonate and potassium phosphate;
catalyst 1 is selected from the group consisting of tetrakis (triphenylphosphine) palladium, palladium acetate and Pd(dppf)Cl$_2$ and Pd$_2$dba$_3$;
the feeding ratio of compound 3 to compound 2 is 0.5-1.6:1;
temperature 2 is 80-120° C.;
time 2 is 2-24 hours;
base 2 is selected from the group consisting of sodium carbonate, potassium acetate, sodium acetate and potassium phosphate;
catalyst 2 is selected from the group consisting of tetrakis (triphenylphosphine) palladium, palladium acetate and Pd(dppf)Cl$_2$ and Pd$_2$dba$_3$;
the feeding ratio of bis(pinacolato)diboron to compound 4 is 0.7-3;
temperature 3 is 10-60° C.;
the feeding ratio of compound 5 to N-chlorosuccinimide is 0.3-3;
temperature 5 is 50-110° C.;
time 5 is 1-20 hours;
base 5 is selected from the group consisting of sodium carbonate, potassium carbonate, palladium carbonate and potassium phosphate;
catalyst 5 is selected from the group consisting of tetrakis (triphenylphosphine) palladium, palladium acetate and Pd(dppf)Cl$_2$ and Pd$_2$dba$_3$;
the feeding ratio of compound 7 to compound 6 is 0.6-1.8;
temperature 6 is 50-110° C.;
time 6 is 2-20 hours;
base 6 is selected from the group consisting of sodium carbonate, potassium carbonate, palladium carbonate and potassium phosphate;
catalyst 6 is selected from the group consisting of tetrakis (triphenylphosphine) palladium, palladium acetate and Pd(dppf)Cl$_2$ and Pd$_2$dba$_3$;
the feeding ratio of compound 9 to compound 8 is 0.6-1.8.

8. The method according to claim 7, wherein temperature 1 is 85-90° C.; time 1 is 4-10 hours; the feeding ratio of compound 3 to compound 2 is 0.7-1.3; temperature 2 is 85-100° C.; time 2 is 10-20 hours; the feeding ratio of bis(pinacolato)diboron to compound 4 is 1.5-2.5; temperature 3 is 20-40° C.; the feeding ratio of compound 5 to N-chlorosuccinimide is 0.5-1.5; temperature 5 is 50-70° C.; time 5 is 1-3 hours; the feeding ratio of compound 7 to compound 6 is 1.2-1.8; temperature 6 is 70-90° C.; time 6 is 14-18 hours; the feeding ratio of compound 9 to compound 8 is 1.2-1.6.

9. The method according to claim 8, wherein temperature 1 is 85° C.; time 1 is 6 hours; the feeding ratio of compound 3 to compound 2 is 0.7; temperature 2 is 95° C.; time 2 is 16 hours; the feeding ratio of bis(pinacolato)diboron to compound 4 is 2.0; temperature 3 is 30° C.; the feeding ratio of compound 5 to N-chlorosuccinimide is 1.0; temperature 5 is 60° C.; time 5 is 2 hours; the feeding ratio of compound 7 to compound 6 is 1.5; temperature 6 is 80° C.; time 6 is 16 hours; the feeding ratio of compound 9 to compound 8 is 1.4.

10. The method according to claim 3:

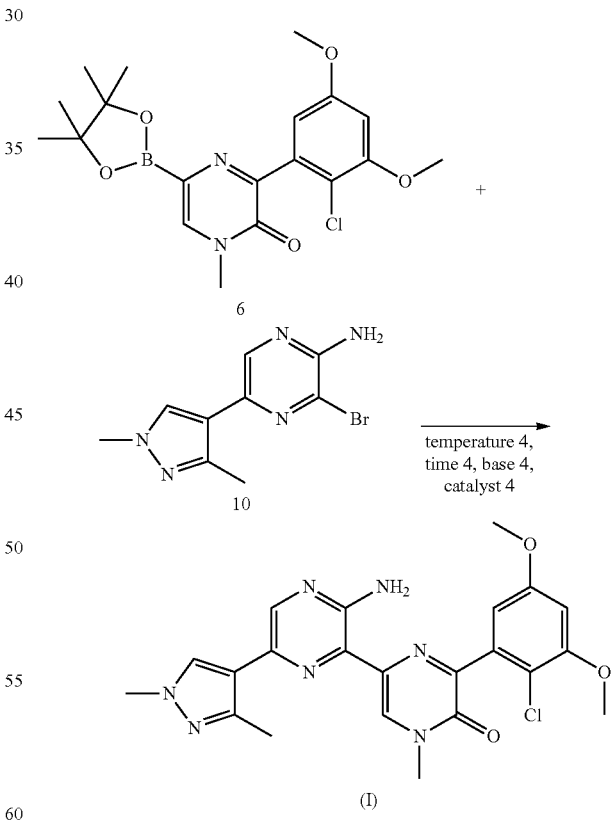

wherein,
temperature 4 is 50-110° C.;
time 4 is 2-20 hours;
base 4 is selected from the group consisting of sodium carbonate, potassium carbonate, palladium carbonate and potassium phosphate;

catalyst 4 is selected from the group consisting of tetrakis (triphenylphosphine) palladium, palladium acetate and Pd(dppf)Cl$_2$ and Pd$_2$dba$_3$;

the feeding ratio of compound 10 to compound 6 is 0.6-1.8.

11. The method according to claim 10, wherein temperature 4 is 85-90° C.; time 4 is 4-10 hours; the feeding ratio of compound 10 to compound 6 is 0.8-1.2.

12. The method according to claim 11, wherein temperature 4 is 100° C.; time 4 is 5 hours; the feeding ratio of compound 10 to compound 6 is 1.0.

* * * * *